(12) United States Patent
Dickey

(10) Patent No.: US 10,342,741 B1
(45) Date of Patent: Jul. 9, 2019

(54) MANAGEMENT AND DISTRIBUTION SYSTEM FOR VITAMINS AND MEDICATION

(71) Applicant: Donald K Dickey, McKinney, TX (US)

(72) Inventor: Donald K Dickey, McKinney, TX (US)

( * ) Notice: Subject to any disclaimer, the term of this patent is extended or adjusted under 35 U.S.C. 154(b) by 94 days.

(21) Appl. No.: 15/369,737

(22) Filed: Dec. 5, 2016

Related U.S. Application Data

(63) Continuation-in-part of application No. 15/187,891, filed on Jun. 21, 2016, now abandoned.

(60) Provisional application No. 62/184,334, filed on Jun. 25, 2015.

(51) Int. Cl.
  *A61J 7/04* (2006.01)
  *A61J 7/00* (2006.01)
  *G07F 11/54* (2006.01)

(52) U.S. Cl.
  CPC .............. *A61J 7/04* (2013.01); *A61J 7/0084* (2013.01); *G07F 11/54* (2013.01)

(58) Field of Classification Search
  CPC .......... A61J 7/04; A61J 7/0084; A61J 7/0481
  See application file for complete search history.

(56) References Cited

U.S. PATENT DOCUMENTS

| | | | | |
|---|---|---|---|---|
| 4,126,247 A | * | 11/1978 | Majka | A61J 7/04 221/2 |
| 4,811,764 A | * | 3/1989 | McLaughlin | A61J 7/0084 141/104 |
| 5,133,478 A | * | 7/1992 | Gordon | A61J 7/0409 221/69 |
| 5,159,581 A | * | 10/1992 | Agans | A61J 7/0481 206/538 |
| 6,733,095 B1 | * | 5/2004 | Rieb | A47B 46/00 312/122 |
| 7,182,218 B2 | * | 2/2007 | Raines | A61J 7/0084 221/101 |
| 2004/0251165 A1 | * | 12/2004 | Girzaitis | A61J 7/04 206/534 |
| 2011/0006074 A1 | * | 1/2011 | Machers | G07F 11/20 221/150 R |
| 2011/0024585 A1 | * | 2/2011 | Brinkdopke | F16B 45/02 248/205.4 |

* cited by examiner

*Primary Examiner* — Gene O Crawford
*Assistant Examiner* — Kelvin L Randall, Jr.
(74) *Attorney, Agent, or Firm* — Eldredge Law Firm, LLC; Richard Eldredge; Beth Felix

(57) ABSTRACT

A medicine container includes a hollow base having a central channel extending therethrough; a sorting assembly slidingly engaged with the base and configured to block passage of the central channel; a dispensing opening extending through the thickness of the hollow base and in communication with the central channel; a first wheel assembly positioned above the base and rotatably relative to the central channel; a first plurality of removable storage modules rotatably and slidingly engaged with the first wheel assembly, the first plurality of removable storage modules are configured to store medicine and dispose of the medicine via the central channel.

4 Claims, 14 Drawing Sheets

MANAGEMENT AND DISTRIBUTION SYSTEM FOR VITAMINS AND MEDICATION

BACKGROUND

1. Field of the Invention

The present invention relates generally to systems for organizing vitamins and medication, and more specifically, to systems for remembering and distributing predetermined dosages of vitamins and medication.

2. Description of Related Art

Medication organization systems are well known in the art and are effective means to distribute predetermined dosages of vitamins and medication. For example, FIGS. 1A and 1B depicts a conventional medication organization system 101 having a container 103 with one or more labeled compartments 105 wherein medicine 109 can be organized by dose per day. On any given day, a user can obtain the predetermined medical dosage 107 for that day by lifting a lid or cover 107 to access the compartment 105.

One of the problems commonly associated with system 101 is there is no method to determine the time of day a pill should be consumed. Also, system 101 becomes increasingly tedious and risky to use as the quantity and diversity of pills increase. For example, an individual with a dosage comprising several large pills will likely consume the entire dose by first dividing the dose into several smaller, more consumable portions—requiring that the individual manually sort each pill. During this manual sorting process, pills are often dropped or misplaced and then not consumed at the prescribed time.

Accordingly, although great strides have been made in the area of medication organization systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1A:
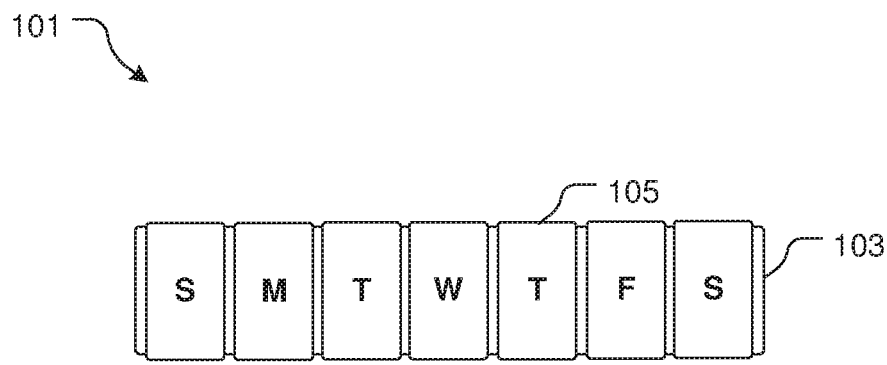
FIG. 1A-1B show top views of a conventional system for remembering and distributing predetermined dosages of vitamins and medication.
Figure 1B:
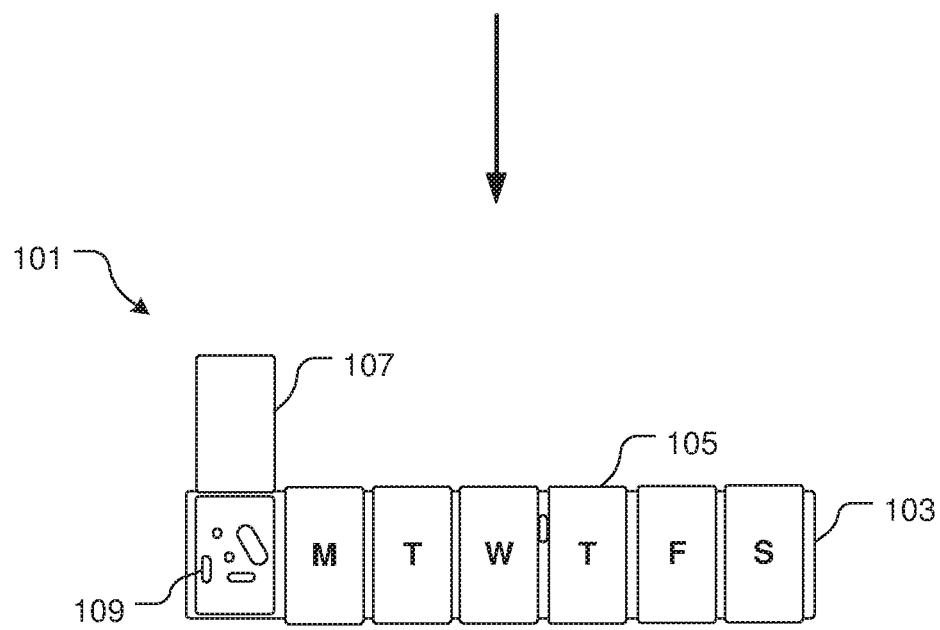

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional medicinal management and distribution systems. Specifically, the present application allows for predetermined medications to be consumed at multiple moments throughout the day. In addition, the present application reduces the risk and tedium of manually sorting large or diverse medications. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
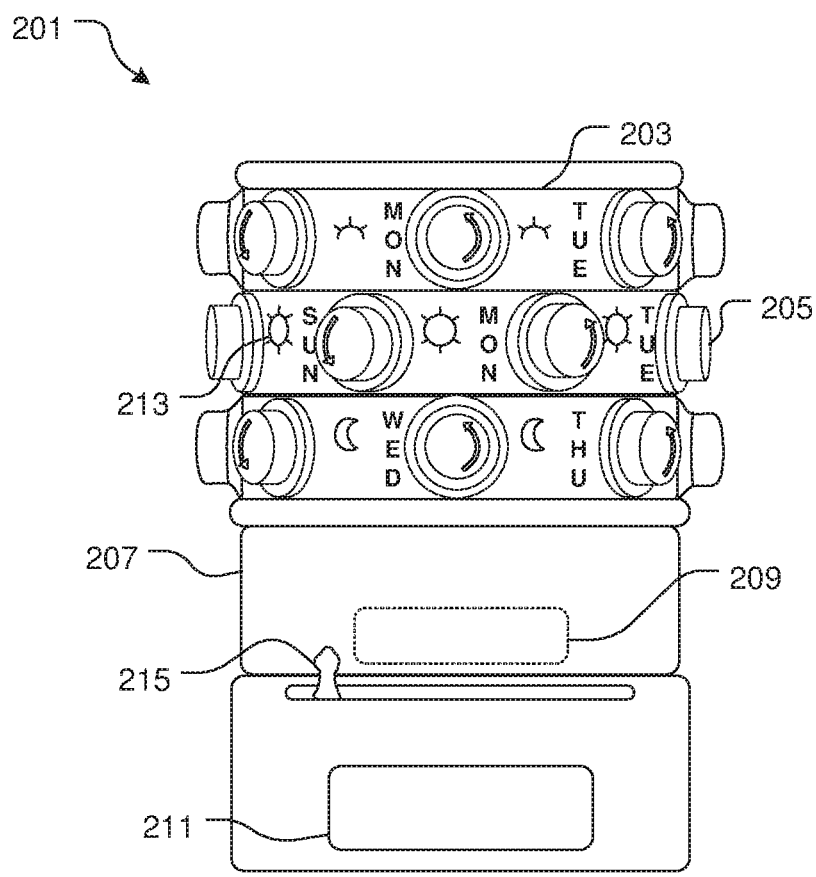
FIG. 2 is a front view of a system for remembering and distributing predetermined dosages of vitamins in accordance with a preferred embodiment of the present application.

Referring now to the drawings wherein like reference characters identify corresponding or similar elements throughout the several views, FIG. 2 depicts a front view of a management and distribution system for vitamins and medicine in accordance with a preferred embodiment of the present application. It will be appreciated that system 201 overcomes one of more of the above-listed problems commonly associated with conventional medicinal management and distribution systems.

In the contemplated embodiment, system 201 includes one or more rotational wheel assemblies 203, each comprising one or more storage modules 205, and a base 207 that is configured with sorting 209 and dispensing 211 assemblies.

It should be appreciated that one of the unique features believed characteristic of the present application is that pills (not shown) can be placed in each storage module 205 and that individual modules 205 and wheel assemblies 203 can represent any defined categories useful for organizing medications. For example, in the preferred embodiment shown, symbols or labels 213 organize three wheel assemblies 203 into morning, afternoon, and evening categories and each assembly 203 includes seven modules 205 labeled for the days of a week. In use, assembly 203 can rotate on base 207 until the module 205 corresponding to the specific date and time of a desired dose can be identified.

Another unique feature believed characteristic of the present application is that module 205 can be rotated to release any pills contained therein through the center of system 201 to the sorting 209 and dispensing assemblies of the base 207. It will be appreciate that base 207 also includes an agitator handle 215 to facilitate the sorting process.

Figure 3A:
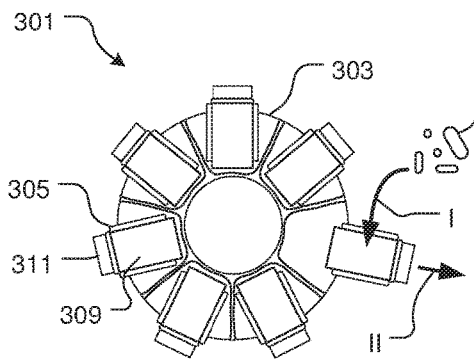
FIGS. 3A-3D show top views of a rotational wheel assembly at various stages of use in accordance with the system of FIG. 2.

Referring now to FIGS. 3A-3D several top views of the rotational wheel assembly of system 201 are shown at various stages of use. FIG. 3A shows the wheel assembly 301 comprising a support structure 303 that houses one or more modules 305 for storing pills 307 in a partially enclosed cavity 309. A knob or handle 311 fixed to each module 305 enables a user to either partially or completely remove module 305 from the support structure 303 and to place pills 306 therein, as depicted by the arrows labeled I and II, respectively.

Figure 3B:
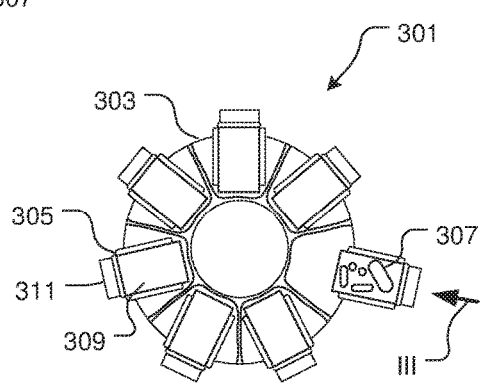
Figure 3C:
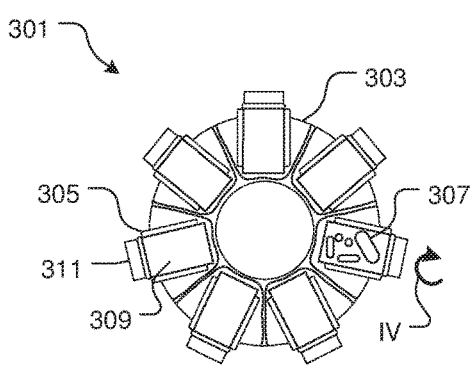
Figure 3D:
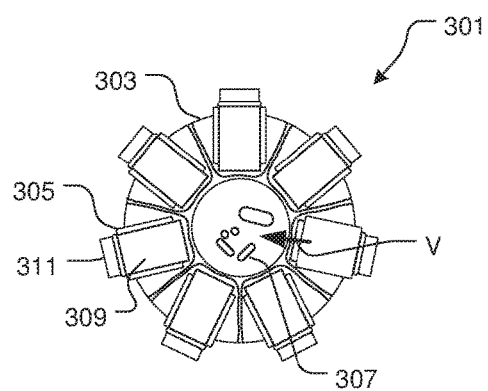

FIGS. 3B, 3C, and 3D respectively show how a recently filled module 305 containing pills 307 is returned to the support structure 303 and the pills 307 deposited, when desired, through the center of the wheel assembly 301 to the sorting and dispensing assemblies of the base (see FIGS. 2 and 4). Once module 305 is returned to the support structure 303, any pills 307 contained therein can be deposited through the center of the wheel assembly 301 by rotating the knob 311, depicted by the arrow labeled IV, until the partially enclosed cavity 309 of module 305 faces sufficiently downwards that the pills 307 fall out, depicted by the arrows labeled III, IV, and V, respectively.

It will be appreciated that knob 311 will be easy to grip and operate and that the contemplated method of use shown in FIGS. 3A-3D is entirely manual. However, alternative embodiments also contemplate automating the method of use disclosed herein or incorporating one or more timers to assist in determining the appropriate time to refill or deposit the contents of module 305.

Figure 4A:
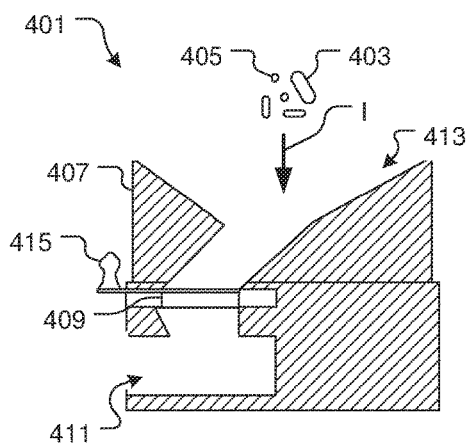
FIGS. 4A-4C depict front, cross-sectional views of the dose distribution and sorting base at various stages of use in accordance with the system of FIG. 2.
Figure 4B:
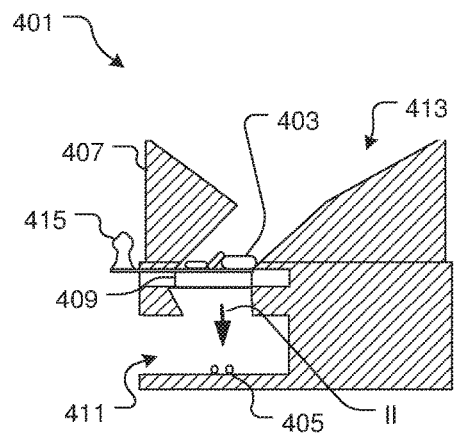
Figure 4C:
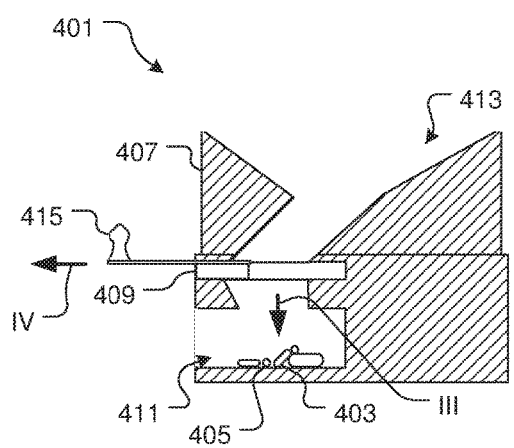

It should be appreciated that one of the unique features believed characteristic of the present application is the ability to manually sort and retrieve large volumes of pills of diverse sizes. Referring now to FIGS. 4A-4C several cross-sectional side views of the sorting and dispensing assemblies of FIG. 2 are shown at various stages of use. In FIG. 4A, and as depicted by the arrow labeled I, larger 403 and smaller 405 pills enter the base 407 of system 201 (see FIG. 2) after being deposited from a storage module (see FIG. 3). One or more sorting means 409, such as a grate or slatted barrier, enables the smaller pills 405 to enter the dispensing assembly 411 while retaining the larger pills 403 within a collection chamber 413, as depicted by the arrow labeled II of FIG. 4B. When desired, use of a handled agitator 415 removes or alters the sorting means 409 such that the larger pills 403 also enter the dispensing assembly 411, as depicted by the arrows labeled IV and III, respectively.

It will be appreciated that the sorting means 409 and dispensing assembly 411 described above can be used not only to partition or sort large quantities of pills deposited from a storage module, but also to sort large volumes of pills directly by pouring them into the base 407 directly via the open center of system 201.

Although only a cavity for dispensing assembly 411 is shown, it is contemplated that dispensing assembly 411 can include either manual or mechanical means for dispensing pills 403 and 405, such as retrievable dose cups or pull-out drawers. It will be appreciated that dispensing pills into dosage cups reduces the risk of human error in losing pills or measuring out incorrect dosage volumes.

Referring now to FIGS. 5-12 in the drawings, a pill distribution system 501 is shown in accordance with an alternative embodiment of the present invention. It will be appreciated that system 501 includes one or more of the features of system 201, and vice-versa.

In the preferred embodiment, the system 501 includes a body 503 with a back surface 505, a front surface 507, a top surface 509, and a bottom surface 511. On top surface 509 is an opening 513 that provides access to the distribution assembly 801 disposed within the inner area formed by body 503. The opening is closed via a lid 515 pivotally attached to body 503 and adapted to open with pressure from the user's hand.

The front surface 507 exposes a plurality of doors 521 accessible to an inner slot 1103. During use, the user places one or more pills within slot 1103 by opening a door 523 pivotally attached to a frame of the distribution assembly 801. It will be appreciated that each door 523 is tailored to assist the user with days of the weeks, e.g., Monday, Tuesday, and so forth along with the time of day, e.g., Morning, Noon, and Night. A graphic such as the moon, full sun and rising sun could also be used as a visual indicator for the time of the day. It is contemplated and will be appreciated that features of the system could have markings to indicate the function or purpose of the feature as depicted on doors 521 and lid 515. It will also be appreciated that these markings could include braille.

Figure 5:
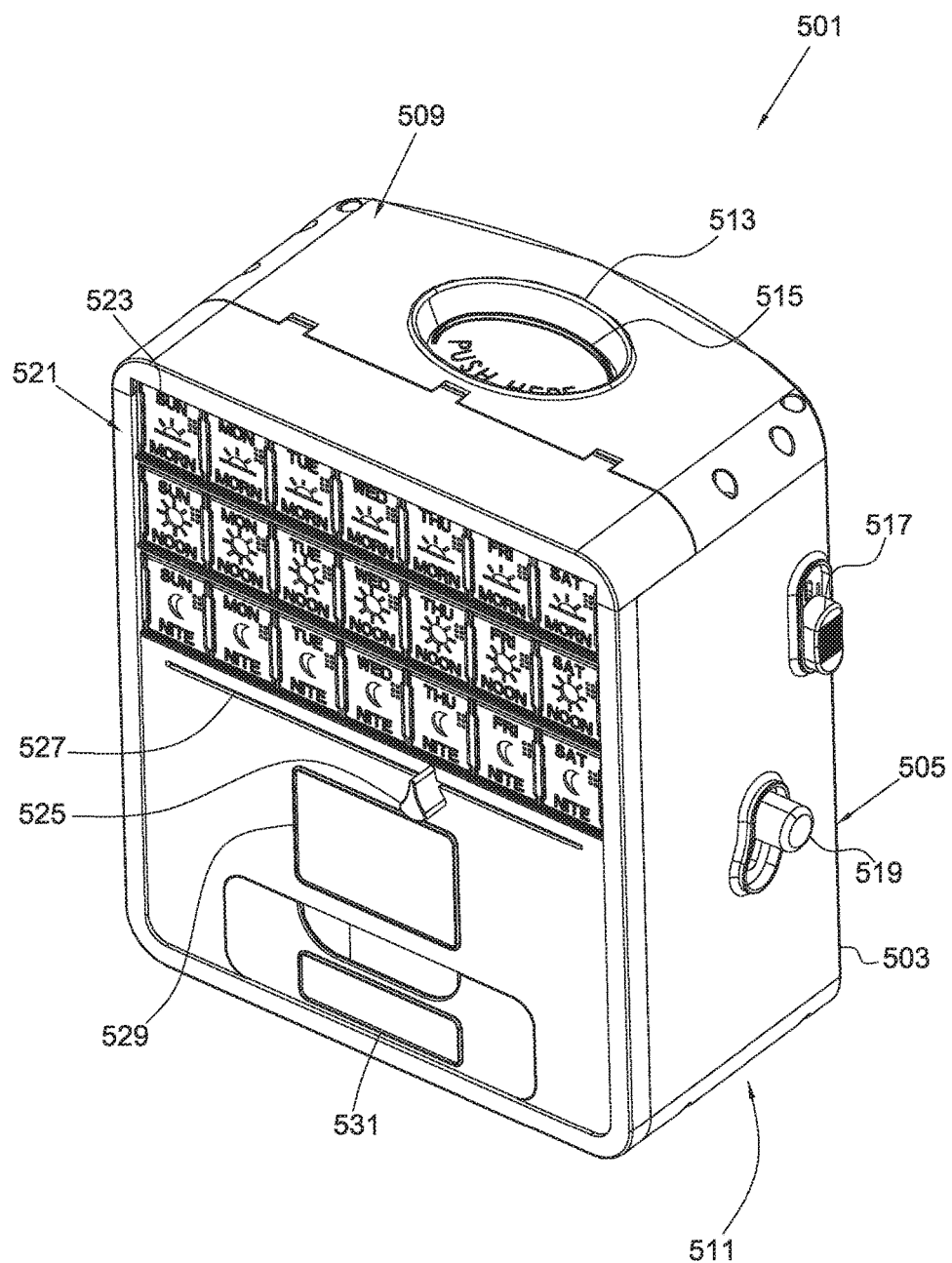
FIG. 5 is an oblique view of a system in accordance with an alternative embodiment of the present application.
Figure 6:
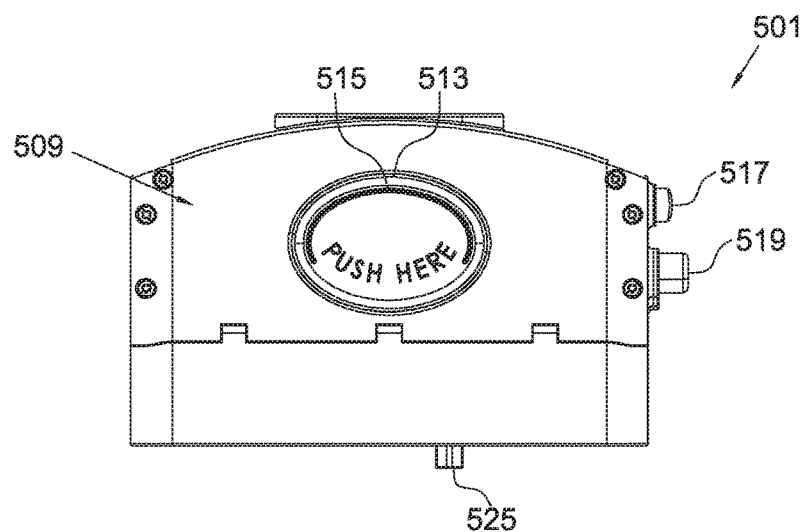
FIG. 6 is a top view of the system of FIG. 5.
Figure 7:
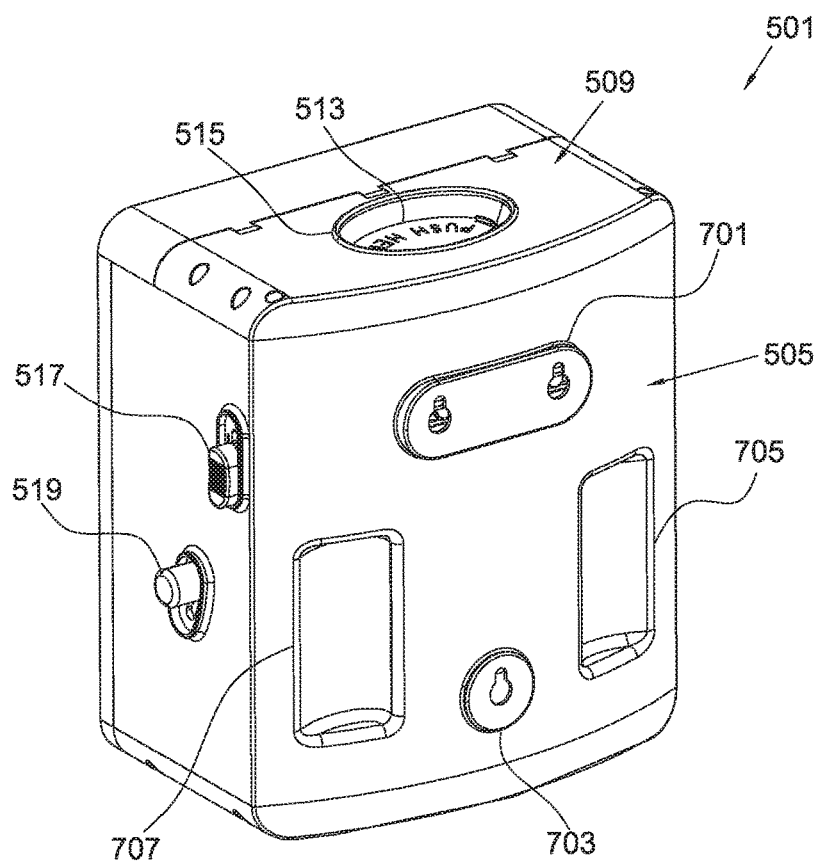
FIG. 7 is a back view of the system of FIG. 5.
Figure 8:
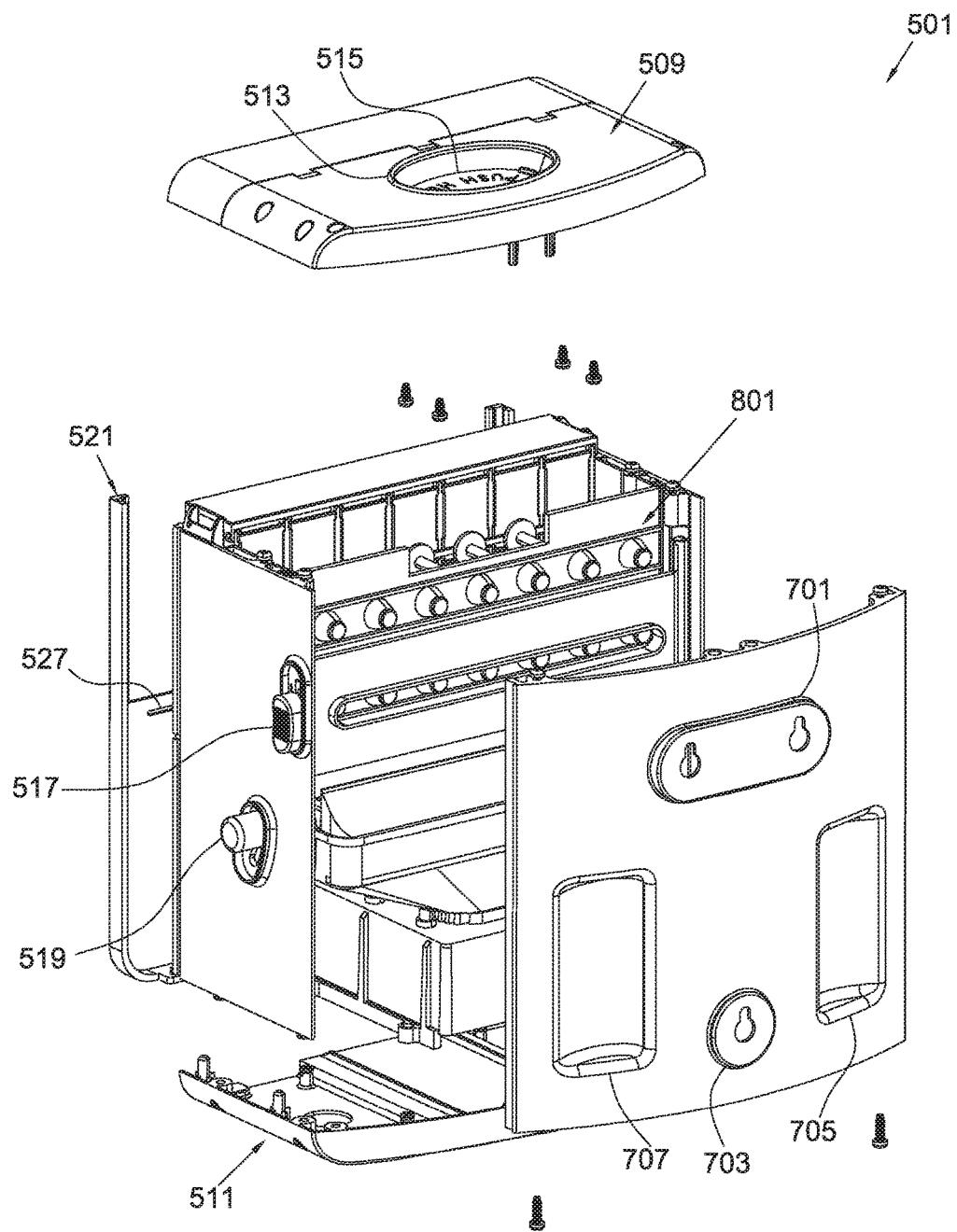
FIGS. 8 and 9 are disassembled views of the system of FIG. 5.
Figure 9:
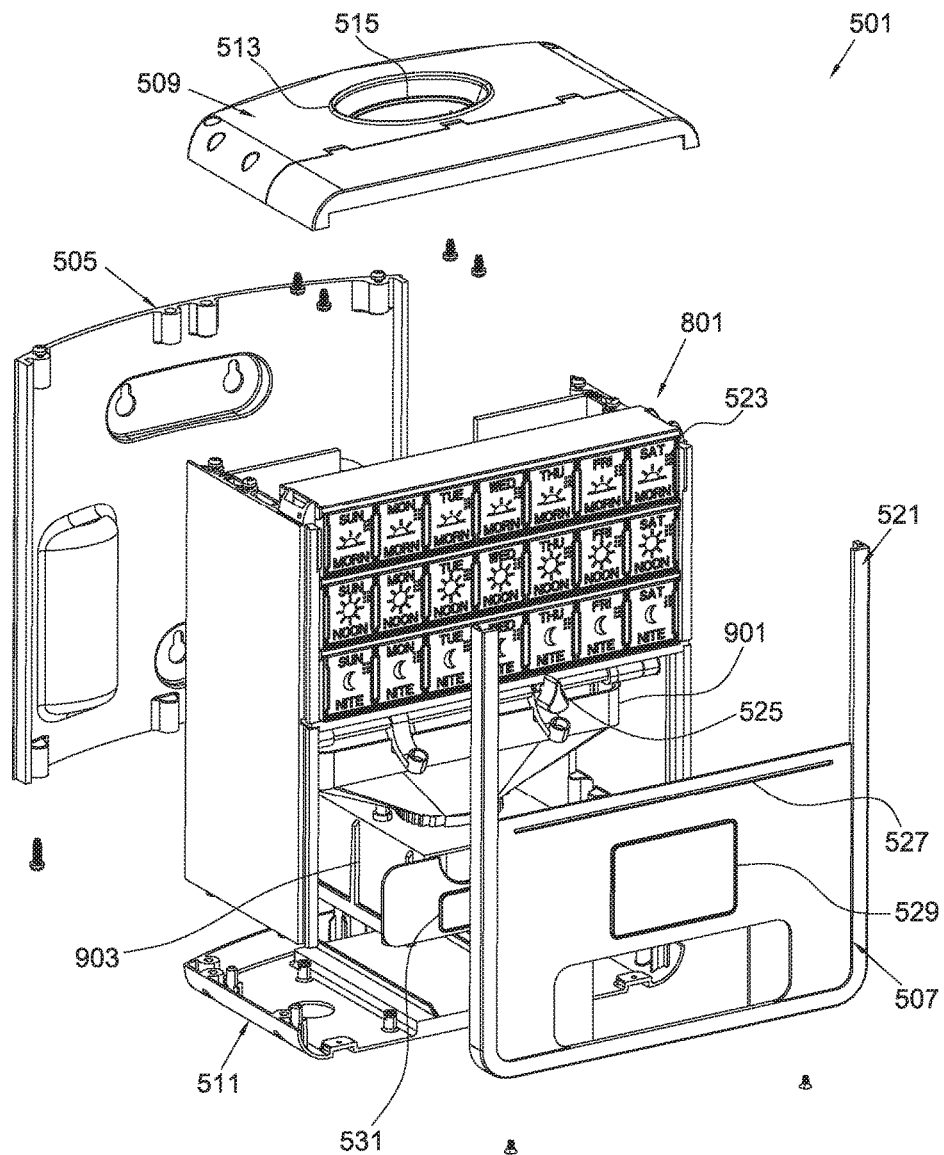
Figure 10:
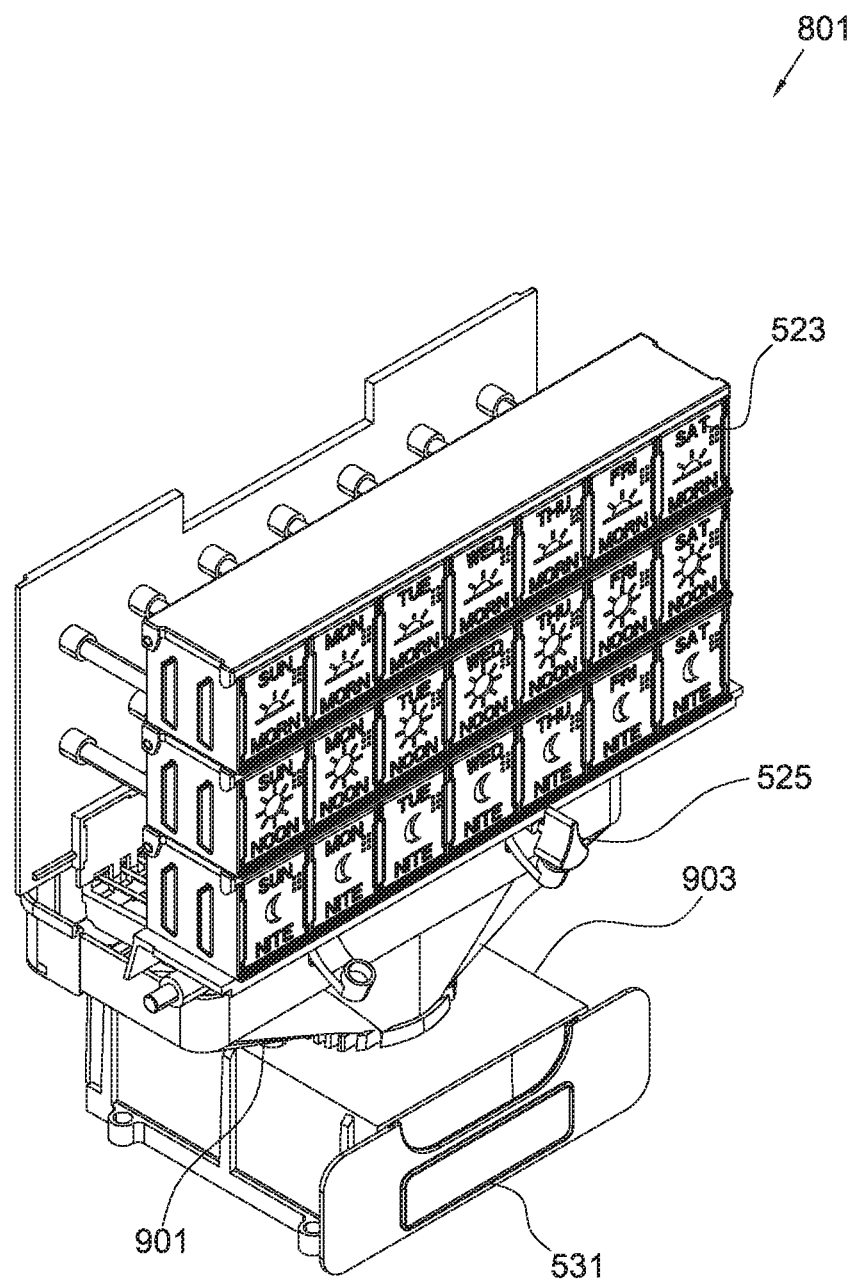
FIG. 10 is an oblique view of a distribution assembly of the system of FIG. 5.
Figures 11, 12:
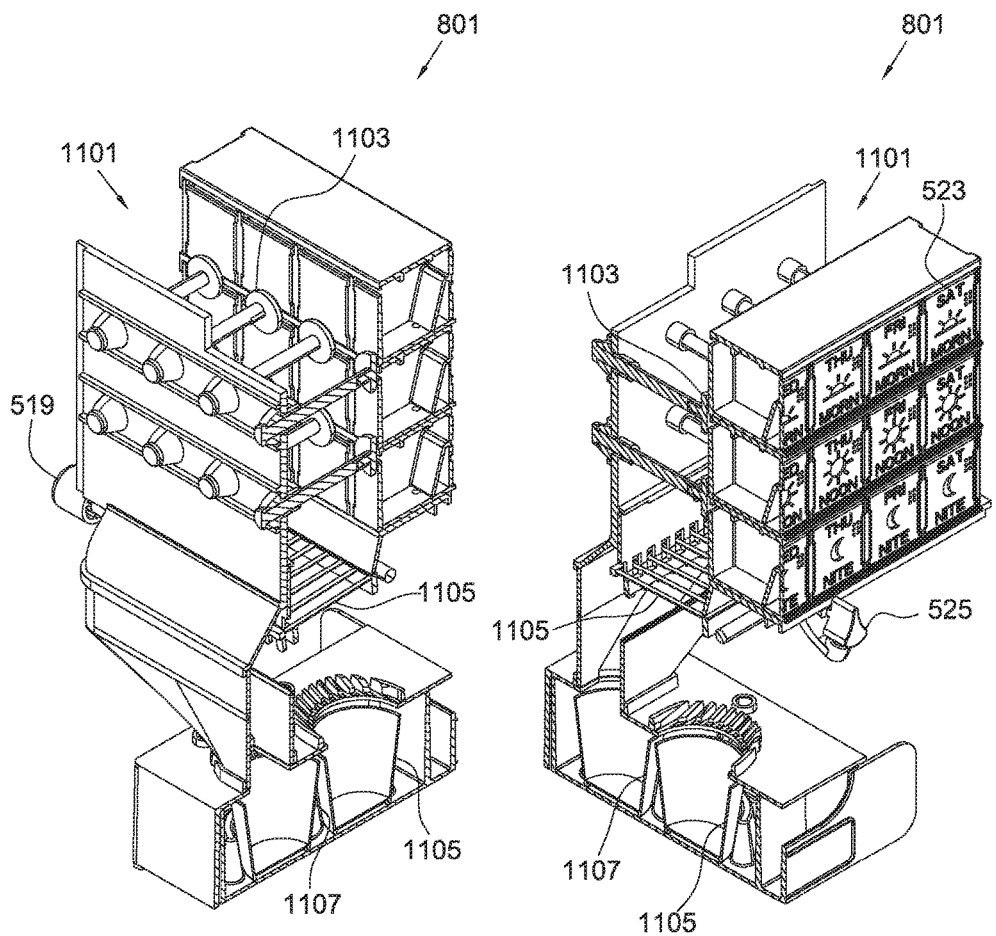
FIGS. 11 and 12 are partial cross-sectional views of the distribution assembly of FIG. 10.
Figure 13:
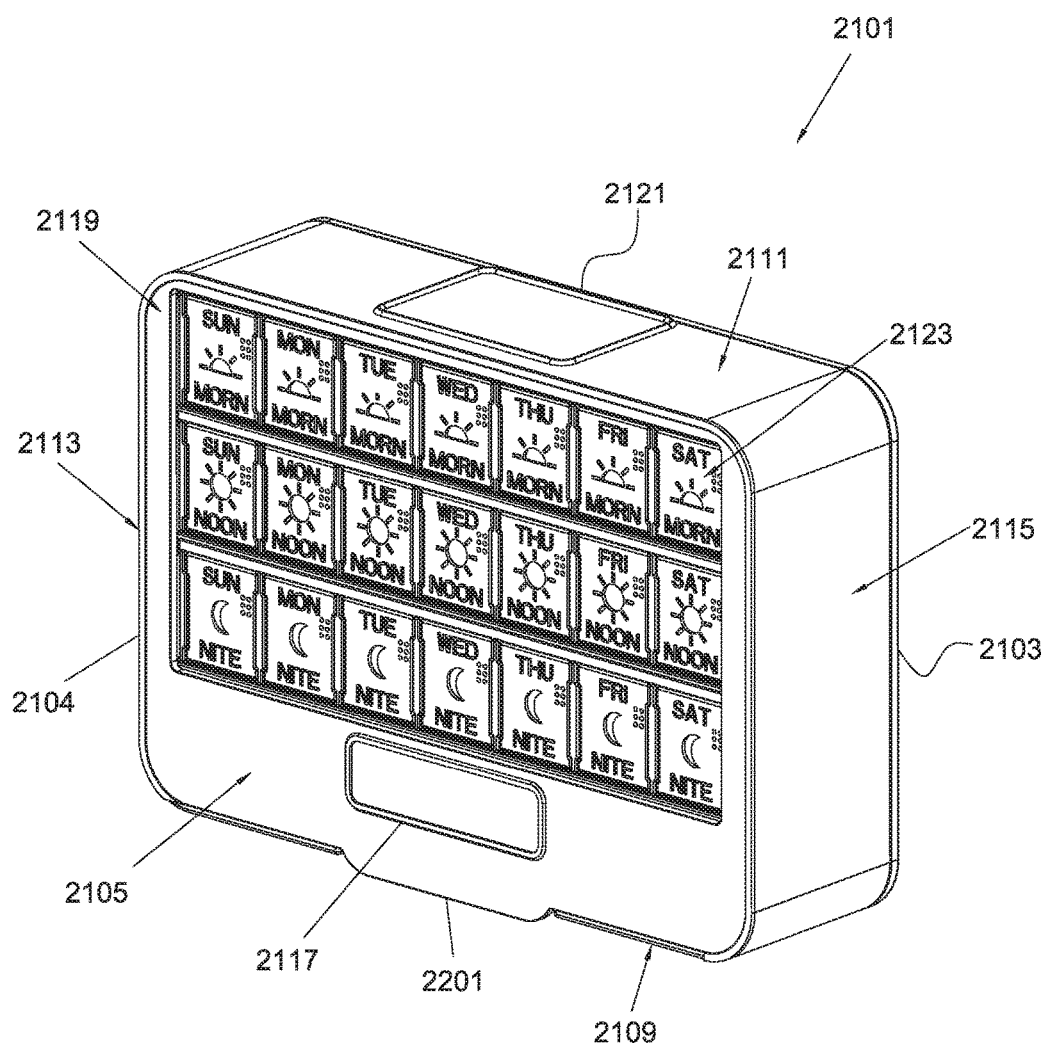
FIGS. 13 and 14A are oblique views of a system in accordance with an alternative embodiment of the present application.
Figure 14A:
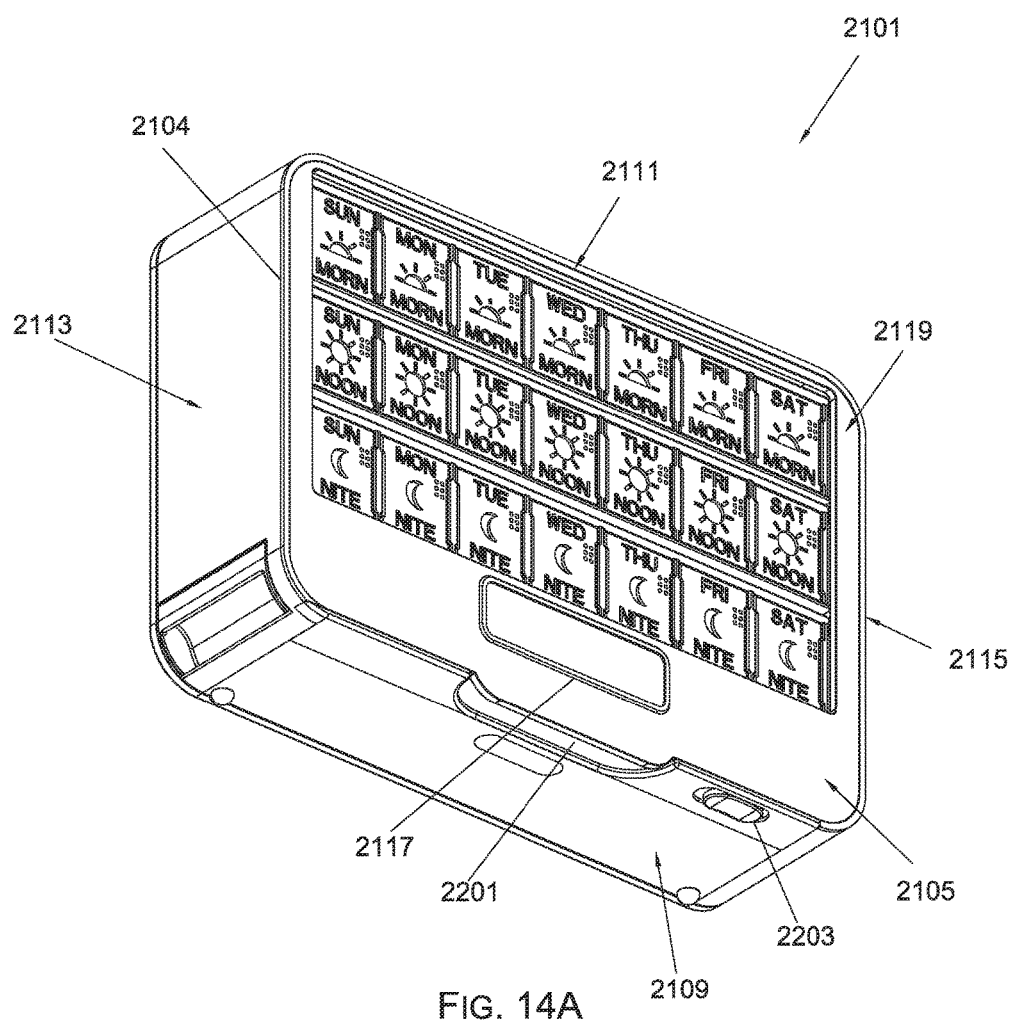
Figure 14B:
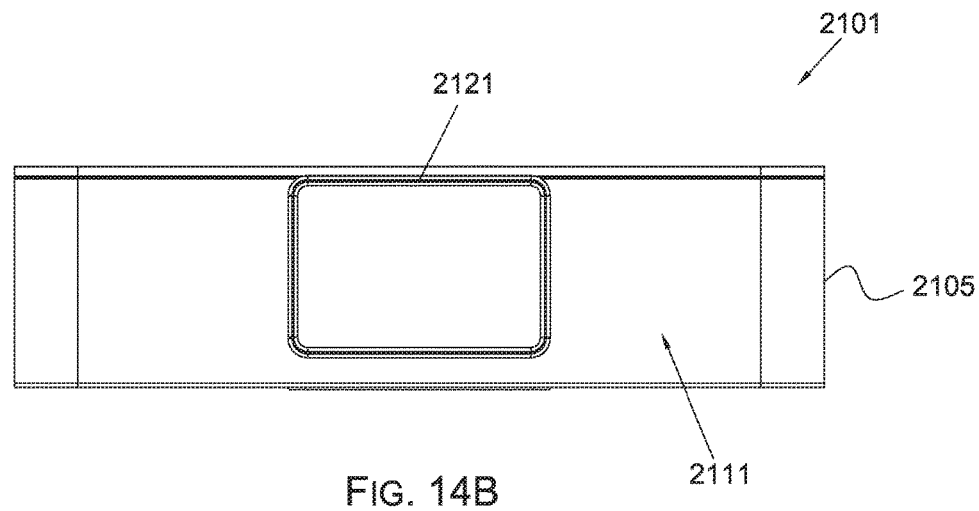
FIG. 14B is a top view of the system of FIG. 13.
Figure 15:
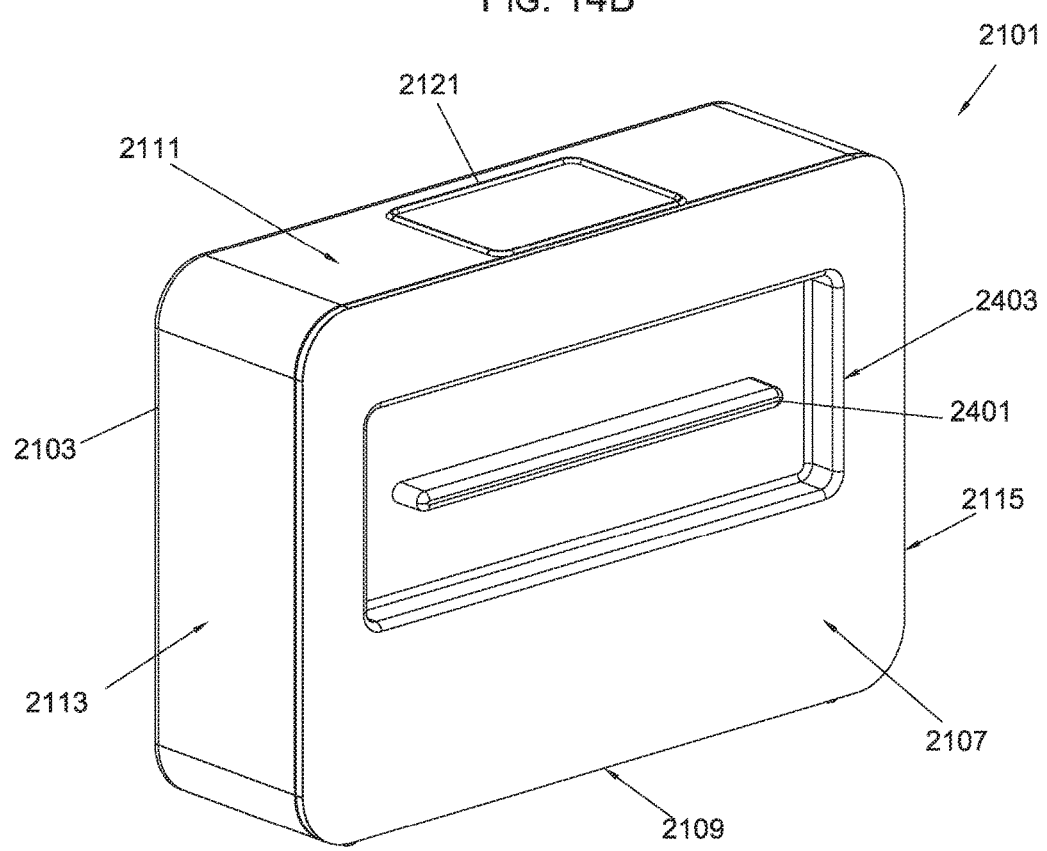
FIG. 15 is a back view of the system of FIG. 13.
Figure 16:
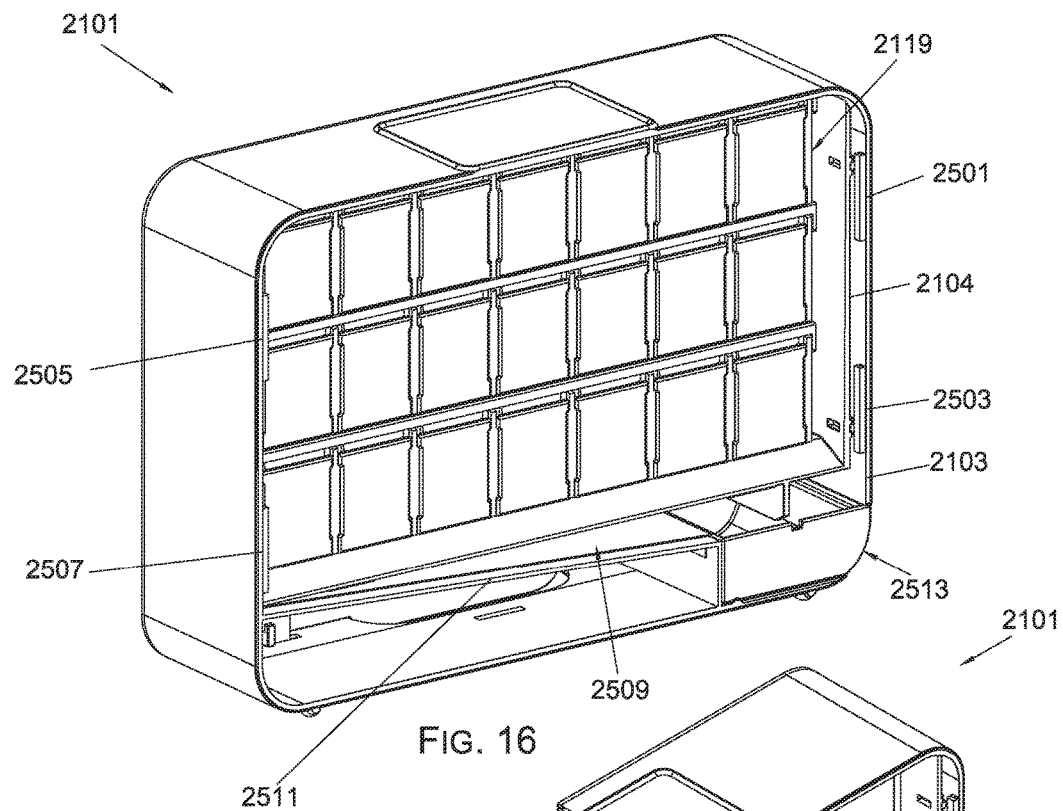
FIG. 16 is a back disassembled view of the system of FIG. 13.
Figure 17:
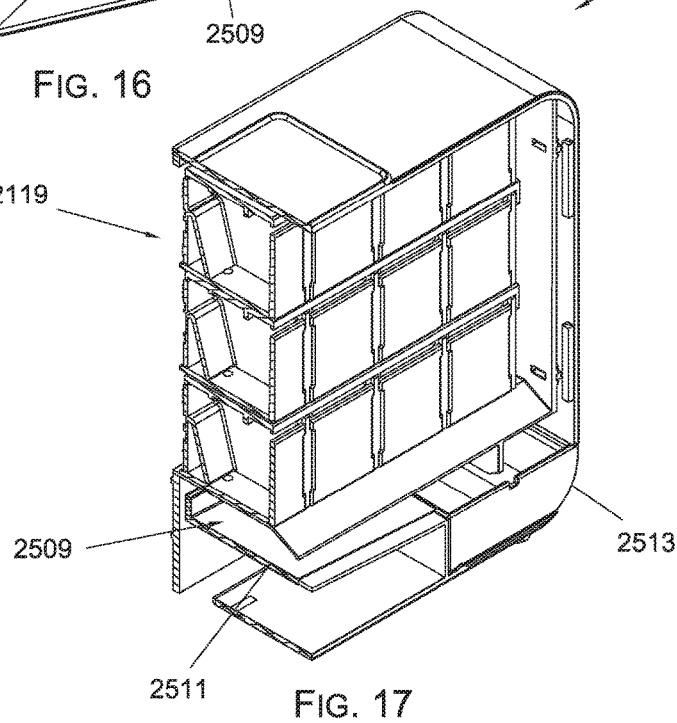
FIG. 17 is a cross-sectional side view of the system of FIG. 16.

The distribution assembly is further provided with levers 517, 519 extending through the surface 505 and operably associated with the components of the distribution assembly 801 for dispersing the pills disposed within the slots to the front openings 529, 531. A slider knob 525 slides within an elongated slot 527 on surface 507 and is configured to indicate a designated row, e.g., Thurs slots, as depicted in FIG. 5.

The back surface 505 is provided with mounting brackets 701, 703 configured to secure the body to a support structure (not shown) via one or more fasteners. The back surface 505 is further provided with one or more indentations 705, 707 extending inwardly from surface 505.

Referring specifically to FIGS. 9-12, the distribution assembly 801 is provided with a chute 901 in communication with an opening 1101 in communication with the slots and configured to channel the pill carried within the slots to a distributing container 903 with one or more cups 1105, 1107 that can be retrieved through opening 531. In the preferred embodiment, the distributing container 903 slidingly engages with the body 503. The assembly 801 is further provided with a grill 1105 for providing additional structural integrity.

An alternative embodiment of the previously discussed pill dispenser system is shown in FIGS. 13-17. System 2101 includes one or more of the system discussed above and further includes the feature of being portable. System 2101 includes a housing 2103 with a pill dispenser frame 2104 slidingly engage within an inner cavity of housing 2103. During use, the pills (not shown) are placed within one or more individual slots of the plurality of slots 2119 labeled from the time of the day and the day of the week on doors 2123 pivotally attached to frame 2104.

The frame 2104 includes a front surface 2105 with a protrusion 2117 extending therefrom and a tab 2201. The housing forms surfaces 2109, 2111, 2113, and 2115 to enclose a space for the frame to fit therein. During assembly, a plurality of brackets 2501, 2503, 2505, and 2507 are utilized to secure the frame in a fixed position, which in turn secures the plurality of slots in a fixed position. The plurality of slots are in communication with an opening 2059 formed by a ramp 2511 configured to direct the pills disposed within each slot to a tray 2513 removably attached to the housing. The system is further provided with a lock tab 2203 configured to secure the frame to the housing. A tab 2401 extending within a cavity 2403 is utilized as means to remove the frame from the housing during use. A tray area 2121 protruding from side 2111 can be utilized to hold the tray in position.

It will be appreciated that one or the unique features believed characteristic of the present invention is the ability to organize, transport, and effectively dispense a plurality of pills during travel.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A pill distribution system, comprising:
  a body having a front surface, a back surface, and a top surface;
  a top opening extending into an inner area of the body from the top surface;
  a plurality of slots extending into the body from the front surface and covered via a plurality of doors, the plurality of slots configured to receive one or more pills, the plurality of doors having a symbol of:
    a rising sun;
    a full sun; and
    a moon;
  a slider knob engaged with an elongated slot on the front surface, the slider knob configured to slide relative to the plurality of doors via the elongated slot;
  an interior opening in communication with each of the plurality of slots within the inner area of the body;
  a single chute extending from the interior opening and having at least two side walls sloping downward, the single chute configured to receive one or more pills from any of the plurality of slots and facilitate dropping of the one or more pills into a distributing container;
  the distributing container positioned underneath the single chute and configured to hold one or more cups;
  a first lever extending from the side of the body and into the inner area of the body to engage with each of the plurality of slots, wherein activation of the first lever releases the one or more pills from one of the slots into the single chute;
  a second lever extending from the side of the body and into the inner area of the body to engage with the single chute, wherein engagement of the second lever allows the single chute to tilt to release the one or more pills into the distributing container; and
  a front opening extending from the front surface of the body and into the distribution container;
  wherein the front opening provides a means for a user to retrieve the one or more pills from the distributing container.

2. The system of claim 1, further comprising:
  a lid pivotally attached to the top surface of the body and configured to cover the opening.

3. The system of claim 1, further comprising:
  one or more mounting brackets attached to the back surface and configured to provide a means to mount the pill distribution system to a wall.

4. The system of claim 1, wherein each of the plurality of slots is associated with a day of the week.

* * * * *